United States Patent
Tao

(10) Patent No.: US 9,090,631 B2
(45) Date of Patent: Jul. 28, 2015

(54) PROCESS FOR PURIFYING CEFOTIAM HYDROCHLORIDE

(75) Inventor: Linggang Tao, Wuyi (CN)

(73) Assignee: HAINAN LINGKANG PHARMACEUTICAL CO., LTD., Hainan (CN)

(*) Notice: Subject to any disclaimer, the term of this patent is extended or adjusted under 35 U.S.C. 154(b) by 0 days.

(21) Appl. No.: 13/997,618

(22) PCT Filed: Apr. 14, 2011

(86) PCT No.: PCT/CN2011/000660
§ 371 (c)(1),
(2), (4) Date: Jun. 24, 2013

(87) PCT Pub. No.: WO2012/126148
PCT Pub. Date: Sep. 27, 2012

(65) Prior Publication Data
US 2014/0011994 A1  Jan. 9, 2014

(30) Foreign Application Priority Data
Mar. 24, 2011  (CN) .......................... 2011 1 0072640

(51) Int. Cl.
*C07D 501/12* (2006.01)
*C07D 501/36* (2006.01)

(52) U.S. Cl.
CPC ............ *C07D 501/12* (2013.01); *C07D 501/36* (2013.01)

(58) Field of Classification Search
CPC .................................................... C07D 501/12
See application file for complete search history.

(56) References Cited

FOREIGN PATENT DOCUMENTS

| CN | 101544662 A | 9/2009 |
| CN | 101633666 B | 8/2010 |
| WO | WO01/83491 A1 | 11/2001 |

*Primary Examiner* — Golam M M Shameem
*Assistant Examiner* — Laura Daniel
(74) *Attorney, Agent, or Firm* — CBM Patent Consulting, LLC

(57) ABSTRACT

A method for treating cefotiam hydrochloride, comprises the following steps: step 1), dissolving the raw material cefotiam hydrochloride in water, treating it with an acidic salt, then cooling it, and filtering the precipitate to obtain an aqueous filtrate; step 2), adding a water-immiscible solvent to the above aqueous solution for extraction, and then separating the organic phase containing impurities to obtain an aqueous solution containing cefotiam hydrochloride; step 3) adding to the aqueous solution a poor solvent of cefotiam hydrochloride and controlling the temperature for recrystallization, washing the educed crystals by centrifugation, and drying them to obtain purified cefotiam hydrochloride. The cefotiam content of the refined cefotiam hydrochloride obtained by the method of the present invention is not less than 86%, the content of polymeric impurities is less than 0.3%, and the content of insoluble microparticles in the injection prepared therefrom is quite low.

7 Claims, 1 Drawing Sheet

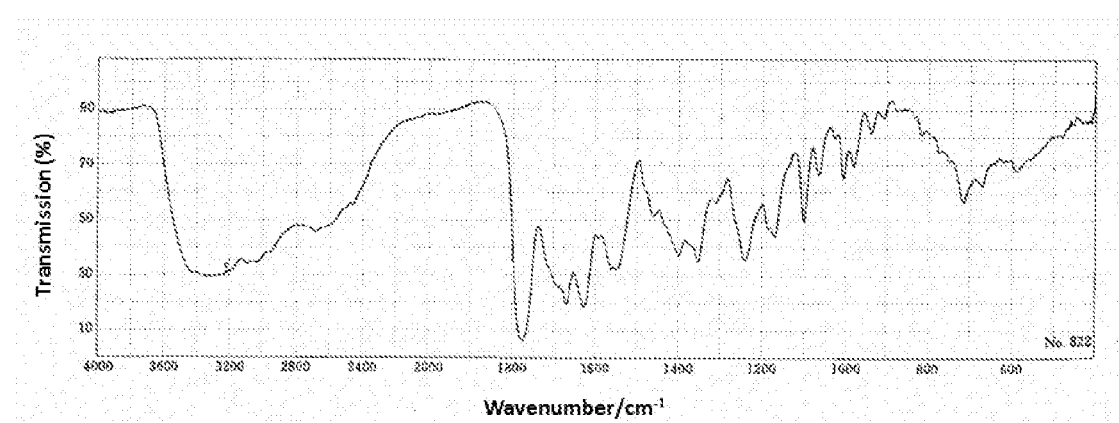

PROCESS FOR PURIFYING CEFOTIAM HYDROCHLORIDE

FIELD OF THE INVENTION

The invention relates to a novel process for purifying cefotiam hydrochloride, and belongs to the medical technical field.

BACKGROUND ART

Cefotiam hydrochloride is a semi-synthetic second-generation cephalosporin and its chemical name is (6R,7R)-7-[[(2-amino-4-thiazolyl)acetyl]amino]-3-[[1-[2-(dimethylamino)ethyl]-1H-tetrazol-5-yl]thiomethyl]-8-oxo-5-thia-1-azabicyclo[4,2,0]oct-2-ene-2-carboxylic acid dihydrochloride. There are many synonyms, for example, cefotiam dihydrochloride, hydrochloride cefotiam, Halospor, Pansporin, Pansporine, Spizef, Sporidyn, Cefapicol, Kemisporin, and Sepidnarin, and the like. Its molecular formula is $C_{18}H_{25}C_{12}N_9O_4S_3$, molecular weight: 598.55, CAS No.: 66309-69-1, a boiling point of 940° C. at 760 mmHg, and flash point: 522.3° C. On an anhydrous basis, the content of cefotiam shall not be less than 79.0%. The structure is as follows:

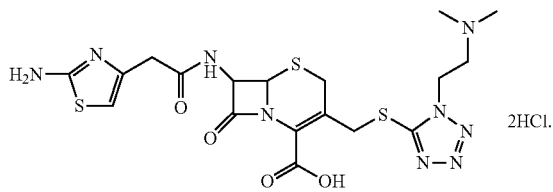 [SMILES: CN(C)CCn1nnnc1SCC1=C(C(=O)O)N2C(=O)C(NC(=O)Cc3csc(N)n3)C2SC1]

Regarding pharmacological toxicology of cefotiam hydrochloride, it is generally believed that its effect on Gram-positive bacteria is similar to that of cefazolin, and its effect on Gram-negative bacteria such as *Haemophilus, Enterobacter, Escherichia coli, Craywhite coli* and *Bacillus mirabilis* is excellent. It also has an antibacterial effect on *Enterobacter, Citrobacter*, and indole-positive *Proteus*. Its mechanism is binding to the penicillin binding proteins (PBPs) on the bacterial cell membrane to acylate transpeptidase, inhibits the synthesis of the septum and cell wall in the bacteria, affects the cross connection of mucopeptide components in the cell wall, and inhibits cell division and growth to make the bacterial morphology long, thereby finally dissolved and dying.

Clinically, cefotiam hydrochloride is mainly used for treating infections caused by sensitive strains, such as pneumonia, bronchitis, biliary tract infections, peritonitis, and urinary tract infections, as well as infections and sepsis after surgery or caused by trauma.

Many domestic and foreign patents and journals have reported the preparation method and purification method of cefotiam hydrochloride.

A method for preparing cefotiam hydrochloride is disclosed by Shanghai Ningrui Biochemical Technology Co., Ltd., which comprising the steps of: (1) introducing dry hydrogen chloride gas after adding the ATA material to a solvent, and then adding a chlorinating agent at a temperature of 0-30° C., and filtering ATC.HCL crystals after the reaction is complete; (2) dissolving 7-ACMT with a base in an aqueous solvent, adding ATC.HCL for acylation reaction at a temperature of −10-35° C., separating the organic solvent after the reaction is over, adding hydrochloric acid to the aqueous phase, adding a hydrophilic solvent whose volume is 3-6 times that of the aqueous layer, and precipitating cefotiam hydrochloride crystals. However, the yield of cefotiam hydrochloride prepared by the method is not high, and solvents such as dichloroethane, acetonitrile, and dimethyl formamide are used during the preparation process, where the residual solvent harms the human body.

The Chinese Patent CN 101633666 B reports a method for synthesizing cefotiam hydrochloride, comprising reacting 2-aminothiazol-4-acetic acid with formic acid to generate 2-formyl-aminothiazol-4-acetic acid, further adding 7-ACMT and triethyl amine, using N,N-diisopropyl-ethylamine and dimethyl formamide as solvents, and p-toluenesulfonyl chloride as a catalyst, stirring the reaction mixture, and then adding hydrochloric acid to obtain the target product. The cefotiam hydrochloride prepared by this method does not have a high purity, and has the problems of poor solvent residues and inconvenient post-treatment and use.

The Chinese patent CN 101544662 discloses a method of preparing a high purity cefotiam hydrochloride by crystallizing cefotiam or its crude salt product. Although this method can improve the purity of cefotiam hydrochloride, it is difficult to separate the inherent purities from the crude drug simply by dissolving, acid adjustment and base adjustment. Moreover, the process of adjusting pH will also bring new negative ion impurities, which increases the difficulty of separation.

Currently, various domestic manufacturers mainly rely on imported crude drugs to obtain cefotiam hydrochloride via dispensing. There are also manufacturers in China preparing such products, but both the yield and purity of the products are low. Accordingly, improving the purity of cefotiam hydrochloride is a problem anxiously to be solved, and has significant social and economic benefits.

DETAILED DESCRIPTION OF THE INVENTION

In order to overcome the above defects of the prior art, in particular to overcome the defect of low purity of cefotiam hydrochloride prepared in the prior art, the present invention provides a process for purifying a cefotiam hydrochloride compound.

Cefotiam hydrochloride to be purified according to the present invention is a cefotiam hydrochloride crude product prepared by the currently known synthesis method, or a commercially available or imported cefotiam hydrochloride crude drug, hereinafter generally referred to as the material cefotiam hydrochloride used in the present invention.

After intensive studies, the inventors find that it is possible to greatly improve the purity of the material cefotiam hydrochloride through a purification method comprising the following processing steps:

step 1), dissolving the raw material cefotiam hydrochloride in water, treating it with an acidic salt, preferably bisulfate, optionally under heating during the treating process, then cooling it, and filtering the precipitate to obtain an aqueous filtrate, which is a primarily purified cefotiam hydrochloride;

step 2), adding a water-immiscible solvent to the above aqueous solution, preferably ethyl acetate, cyclohexane or a mixture of ethyl acetate and cyclohexane, for extraction, and then separating the organic phase containing impurities to obtain a secondarily purified aqueous solution containing cefotiam hydrochloride; and step 3), adding to the aqueous solution a poor solvent of cefotiam hydrochloride, preferably ethanol or acetone, and controlling the temperature for recrystallization, washing the educed crystals by centrifugation, and drying them to obtain a thirdly purified cefotiam hydrochloride.

The present invention is described in detail by the following embodiments.

Step 1)

Dissolving the raw material cefotiam hydrochloride in water, treating it with an acidic salt, preferably bisulfate, optionally under heating during the treating process, then cooling it, and filtering the precipitate to obtain an aqueous filtrate, which is a primarily purified cefotiam hydrochloride.

Said bisulfate is preferably a bisulfate of an alkali metal, more preferably sodium bisulfate or potassium bisulfate.

The treatment is optionally carried out under heating, preferably at a temperature of 20-50° C., more preferably 30-45° C., most preferably 40° C. If the temperature is too high, it may easily lead to unnecessary decomposition of organic substances; and if the temperature is greater than 50° C., the cefotiam hydrochloride may undergo degradation and polymerization reactions, resulting in a reduced content of the pharmaceutically active ingredient, color enhancement, an increased content of polymeric impurities.

The time for the treatment generally ranges from several minutes to several hours, preferably from 30 minutes to 5 hours, more preferably from 1 hour to 3 hours, and most preferably 2 hours.

After the above treatment, a few precipitates would come out. As the temperature decreases, the precipitated amount would be increased.

Without being bound by any theory, step 1) of the present invention employs acidic salts to treat cefotiam hydrochloride, which achieves the effect of purification possibly for the following reasons:

The final step for many methods of obtaining cefotiam hydrochloride is the removal of the carboxyl protecting group, e.g., ester group is a common protecting group of a carboxyl group, and this will inevitably lead to the presence of a small amount of ester impurities in the crude product of cefotiam hydrochloride. The presence of an acidic salt such as bisulfate contributes to the hydrolysis of the residual ester materials into cefotiam hydrochloride, which not only effectively reduces impurities but also increases the yield of the target product. Further, as stated in CN 101544662, cefotiam hydrochloride, during storage, particularly when the temperature is greater than 50° C., tend to undergo degradation and polymerization reactions, resulting in reduced content of pharmaceutically active ingredient, color enhancement, and elevated levels of polymeric impurities. After treatment by the steps of the present invention, it helps to precipitate these polymeric impurities and other insoluble impurities so as to be separated from cefotiam hydrochloride.

Step 2)

Adding to the above-described aqueous solution a water-immiscible solvent or solvent mixture for extraction, and then separating the organic phase to obtain a secondarily purified aqueous solution containing cefotiam hydrochloride.

The organic solvent is preferably ethyl acetate, cyclohexane, or a solvent mixture formed from ethyl acetate and cyclohexane, more preferably ethyl acetate.

The organic solvent is used in an amount of preferably less than half of the aqueous solution, more preferably less than one-third of the aqueous solution. Repeated extraction can be carried out, preferably the extraction is carried out for 2 to 3 times. To achieve full extraction, stirring is preferably carried out. The organic phase containing impurities is then removed by liquid separation.

Extraction is used for the following reasons: under normal circumstances, the raw material cefotiam hydrochloride typically contains a solvent introduced in the preparation process, a variety of raw materials and intermediates, moisture carried in due to hygroscopicity, a bacterial endotoxin, as well as a variety of inorganic substances and heavy metals. These substances are present in the form of impurities, affecting the purity of the raw cefotiam hydrochloride. We note that these substances are present in a very low amount, and are still dissolved in the aqueous solution of cefotiam hydrochloride with a trace amount. However, the solubility of these substances in the organic solvent is greater, and extraction is a common separation method with good effects.

Step 3)

Adding to the aqueous solution a poor solvent of cefotiam hydrochloride, preferably ethanol or acetone, and controlling the temperature for recrystallization, washing the educed crystals by centrifugation, and drying them to obtain a thirdly purified cefotiam hydrochloride.

We found that, by the common method of reflux-recrystallization in a solvent(s) or reflux-suspension under stirring in a solvent(s), it is hard for cefotiam hydrochloride to be crystallized, or impurities are entrained in the precipitated cefotiam hydrochloride. However, direct treatment of crude cefotiam hydrochloride by a good-poor solvent(s) precipitation method cannot achieve the expected purity, either.

The solubility of cefotiam hydrochloride is great in water but very small in ethanol, and even smaller in acetone. A mixture of water and ethanol or a mixture of water and acetone is used as the solvent to recrystallize cefotiam hydrochloride.

Surprisingly, after treatment by the above steps 1) and 2) of the present invention, crystals with a very high purity can be obtained by using a mixture of water and ethanol or a mixture of water and acetone in an appropriate proportion as the solvent to dissolve cefotiam hydrochloride for recrystallization.

The reason may lied in that, the steps 1) and 2) of the present invention have removed impurities that have an adverse effect on recrystallization, and the cefotiam hydrochloride product treated with bisulfate is more suitable to be recrystallized and precipitated from such a mixed solvent.

When recrystallization is carried out, the aqueous cefotiam hydrochloride obtained in the step 2) is firstly concentrated at an elevated temperature such as 20-50° C., thereby reducing the water content, and then ethanol is added according to the volume ratio 3:7 of water to ethanol, or acetone is added according to the volume ratio 4:6 of water to acetone, said ratio referring to the ratio of the volume of ethanol or acetone to the volume of water in the above concentrated solution. And then the temperature is slowly reduced to be between room temperature and 5° C., where crystals are precipitated slowly during this process. Optionally, cefotiam hydrochloride seed crystals are introduced during the cooling process. After standing 5-48 hours, crystallization is complete, followed by air drying or drying in an oven, preferably air drying.

BRIEF DESCRIPTION OF THE DRAWINGS

FIG. 1 is an infrared absorption spectrum of the refined cefotiam hydrochloride obtained in the example.

EMBODIMENTS OF THE INVENTION

The present invention provides a process for purifying cefotiam hydrochloride, characterized in that it comprises the following steps:

step 1), dissolving the raw material cefotiam hydrochloride in water, treating it with bisulfate under heating, preferably at a temperature of 20-50° C. for a time ranging from several minutes to several hours, preferably from 30 minutes to 5 hours, then cooling it, filtering the precipitated precipitates to obtain an aqueous filtrate;

step 2), adding to the aqueous filtrate ethyl acetate, cyclohexane, or a mixture of ethyl acetate and cyclohexane under stirring for extraction several times, where each time preferably the amount of the organic solvent is less than half of the aqueous solution, and then separating the organic phase to obtain an aqueous solution containing cefotiam hydrochloride; and step 3), concentrating the aqueous solution of cefotiam hydrochloride obtained from the step 2) at an elevated temperature, such as 20-50° C., and then adding to the aqueous solution ethanol or acetone, slowly cooling the mixture for recrystallization; allowing the crystals to precipitate after standing 5-48 hours; washing the educed crystals by centrifugation, and obtaining purified cefotiam hydrochloride by air drying or drying in an oven.

In one embodiment of the present invention, the bisulfate described in step 1) is preferably a bisulfate of an alkali metal, more preferably sodium bisulfate or potassium bisulfate.

In one embodiment of the present invention, the processing temperature described in step 1) is 30-45° C., preferably 40° C. The processing time ranges from 1 hour to 3 hours, preferably 2 hours.

In one embodiment of the present invention, in the step 2), the organic solvent is ethyl acetate.

In one embodiment of the present invention, in the step 2), the organic solvent for each extraction is in an amount less than one-third of the aqueous solution, and the extraction is carried out twice or three times.

In one embodiment of the present invention, in the step 3), ethanol is added according to the volume ratio 3:7 of water to ethanol, or acetone is added according to the volume ratio 4:6 of water to acetone.

In one embodiment of the present invention, in the step 3), after adding a solvent, the temperature is reduced to be between room temperature and 5° C.

In one embodiment of the present invention, in the step 3), cefotiam hydrochloride seed crystals are introduced during the cooling process, and the educed crystals are dried by airing.

In the refined cefotiam hydrochloride obtained in the above embodiments, as determined in accordance with the high-performance liquid chromatography (Chinese Pharmacopoeia, edition of 1995, Part II, Appendix VD), the content of cefotiam is not less than 86%, typically not less than 87%. The content of polymer impurities is generally less than 0.3%, typically less than 0.1%. The content of insoluble particles in the injection prepared therefrom is low.

The powder flowability, characteristic dissolution rate, solid stability, and process operability of cefotiam hydrochloride have a great impact on the activity and the preparations formulated, and the dissolution rate, formulability and stability of the cefotiam hydrochloride which is greatly improved in purity are also corresponding improved.

Thus, the cefotiam hydrochloride purified according to the process of the present invention is entirely suitable to be formulated into an antibacterial pharmaceutical composition for the treatment of infections caused by sensitive strains, such as pneumonia, bronchitis, biliary tract infections, peritonitis, and urinary tract infection, as well as infections and sepsis after surgery or caused by trauma. Said pharmaceutical composition comprises the cefotiam hydrochloride purified according to the process of the present invention and a pharmaceutically acceptable excipient. Optionally, the pharmaceutical composition may be a lyophilized powder ampul, or a preparation for injection.

The present invention also provides use of the above pharmaceutical composition in the preparation of a medicament for the treatment of infections caused by sensitive strains as well as the infections and sepsis after surgery or caused by trauma. Preferably, the infections include pneumonia, bronchitis, biliary tract infections, peritonitis, and urinary tract infection.

The present invention fundamentally changes the worldwide status of low purity of cefotiam hydrochloride materials, solves the difficulties encountered by crude cefotiam hydrochloride and cefotiam hydrochloride materials, and improves a series of clinical adverse reactions caused by too much insoluble microparticles or polymer impurities. The method of the present invention is also simple, easy to control and of industrial production.

The present invention is further explained or described by the following examples. However, the examples provided shall not be construed as limiting the protective scope of the present invention.

I. HPLC Determination of the Purity of Cefotiam Hydrochloride

Instruments and Reagents: Agilent1100 type high performance liquid chromatography. Water was re-distilled water. Acetonitrile was HPLC grade. Cefotiam hydrochloride reference (National Institute for Food and Drug Control, batch number: 1000012200504, purity >99%); cefotiam hydrochloride powder ampul for injection (Shanghai ASIA Pioneer Pharmaceutical Co., Ltd., Specification: 1.0 g per bottle); cefotiam hydrochloride sample was obtained by purification according to the process of the present invention.

Chromatographic conditions: chromatographic column was DiamonsilTMC18 (4.6 mm×250 mm, 5 μm); mobile phase was phosphate buffer solution (to 0.05 mol/L disodium hydrogen phosphate solution was added 0.05 mol/L potassium dihydrogen phosphate solution to adjust pH as 7.6 to 7.8 (the capacity ratio was about 4:1))-acetonitrile (88:12); the flow rate was 1.0 mL/min; detection wavelength was 254 nm; column temperature was 25° C.; injection volume was 20 μL; the retention time of cefotiam hydrochloride was about 14 minutes.

The specific procedure is as follows: to a suitable amount of cefotiam hydrochloride sample, a mobile phase was added to prepare a 1 mg/ml solution as a test solution; to a precisely weighed amount of the reference, a mobile phase was added to prepare a 0.01 mg/ml solution as a control solution. 10 microliters of the control solution was loaded into the liquid phase chromatograph. The detection sensitivity was adjusted, making the peak height of the principal component peak be 10% to 15% of the full scale. Then a precisely weighed amount of 10 microliters of the test solution and the control solution were loaded into the liquid phase chromatograph, respectively. The chromatograms were recorded till it reached 2 times of the retention time of the principal component peak. The content of cefotiam in the sample was calculated by an external standard method.

II. Determination of the Content of Polymer:

The content of polymer impurities in the cefotiam hydrochloride sample was determined using the Sephadex G-10 gel chromatography system.

Example 1

10 g of crude cefotiam hydrochloride prepared in accordance with CN 101633666 B was taken, where the content of cefotiam measured by High Performance Liquid Chromatography was 75%, and the content of polymers measured by the gel chromatography system was 3%. The crude cefotiam hydrochloride was dissolved in 200 ml water, treated with 20 ml of 1M sodium bisulfate aqueous solution at a temperature of 30° C. for 2 hours. Then the mixture cooled down to room temperature and precipitated. An aqueous filtrate was obtained after filtration.

Ethyl acetate was added to the above aqueous solution for extraction twice, where each time the solvent used accounted for 40% of the volume of said aqueous solution. The mixture was sufficiently stirred, allowed to stand, and then the organic phase was separated to obtain an aqueous phase containing cefotiam hydrochloride.

The aqueous solution of cefotiam hydrochloride obtained was warmed to 45° C. for concentration. The solution was concentrated to a volume of 150 ml, and then ethanol was added to the aqueous solution at a volume ratio of ethanol to water of 3:7. It slowly cooled to 15° C. for recrystallization. Crystals were precipitated and allowed to stand for 10 hours until no further crystals were precipitated. The mixture was centrifuged with a centrifuge, and then filtered. The filter cake is washed with analytically pure ethanol, and air-dried to give 9.5 g white cefotiam hydrochloride with a yield of 95%. FIG. 1 is an infrared absorption spectrum of the refined cefotiam hydrochloride.

The content of cefotiam measured by High Performance Liquid Chromatography was 87.2%, and the content of polymer impurities measured by the gel chromatography system was less than 0.1%. To the purified product water was added to prepare a solution of about 0.1 g per 1 ml, which was clear and colorless, with approximately 500 insoluble microparticles having a diameter greater than or equal to 10 μm.

Comparative Example 1

In accordance with the purification method described in the Chinese Patent CN 101544662, crude cefotiam hydrochloride employed in Example 1 was purified. The content of cefotiam measured by High Performance Liquid Chromatography was 80.2%, and the content of polymers measured by a molecular exclusion method was 1%.

Example 2

10 g cefotiam hydrochloride crude drug (JiangSu jiuzhitang Biological Products Co., Ltd., year of production: August 2010) was taken, where the content of cefotiam measured by High Performance Liquid Chromatography was 79.5%, and the content of polymers measured by a molecular exclusion method was 0.5%. The crude cefotiam hydrochloride was dissolved in 150 ml water, treated with 15 ml of 2M aqueous potassium bisulfate at a temperature of 40° C. for 1 hour, and then cooled to room temperature. A small amount of precipitates came out, and an aqueous filtrate was obtained after filtration.

To the above aqueous solution, cyclohexane was added for extraction three times, where each time the volume of the solvent used accounted for 30% of the volume of the aqueous solution. The mixture was sufficiently stirred, and allowed to stand. Then the organic phase was separated to obtain an aqueous phase containing cefotiam hydrochloride.

The cefotiam hydrochloride aqueous solution obtained was warmed to 48° C. for being concentrated into a solution volume of 100 ml. Then acetone was added to the aqueous solution at a 4:6 volume ratio of acetone to water. A few cefotiam hydrochloride seed crystals were introduced into the mixture. The mixture slowly cooled to 10° C. for recrystallization. Crystals were precipitated. The mixture was allowed to stand for 15 hours until no further crystals were precipitated. The mixture was centrifuged with a centrifuge, and filtered. The filter cake was washed with acetone, dried in vacuum at 30° C. to obtain 9.6 g white cefotiam hydrochloride with a yield of 96%.

The content of cefotiam measured by High Performance Liquid Chromatography was 87.1%, and the content of polymer impurities measured by the gel chromatography system was less than 0.1%. To the purified product, water was added to prepare a solution of about 0.1 g per 1 ml, which is clear and colorless, with approximately 400 insoluble microparticles having a diameter greater than or equal to 10 μm.

Example 3

10 g cefotiam hydrochloride crude drug (Shanghai ASIA Pioneer Pharmaceutical Co., Ltd., batch number 20080912) was taken, where the content of cefotiam measured by High Performance Liquid Chromatography was 77.5%, and the content of polymer measured by a molecular exclusion method was 2.5%. The cefotiam hydrochloride crude product was dissolved in 250 ml water, treated with 30 ml of 1M aqueous potassium bisulfate at a temperature of 35° C. for 3 hours, and then cooled to room temperature. A small amount of precipitates came out, and an aqueous filtrate was obtained after filtration.

To the above aqueous solution a mixed solvent of 1:1 cyclohexane and ethyl acetate was added for extraction three times, where each time the volume of the solvent used accounted for 25% of the volume of the aqueous solution. The mixture was sufficiently stirred, and allowed to stand. Then the organic phase was separated to obtain an aqueous phase containing cefotiam hydrochloride.

The cefotiam hydrochloride aqueous solution obtained was warmed to 40° C. for being concentrated into a solution volume of 150 ml. Then anhydrous ethanol was added to the aqueous solution at a 3:7 volume ratio of ethanol to water. A few cefotiam hydrochloride seed crystals were introduced into the mixture. The mixture slowly cooled to 8° C. for recrystallization. Crystals were precipitated, The mixture was allowed to stand for 12 hours until no further crystals were precipitated. The mixture was centrifuged with a centrifuge, and filtered. The filter cake was washed with anhydrous ethanol, and dried in vacuum at 35° C. to obtain 9.55 g white cefotiam hydrochloride with a yield of 95.5%.

The content of cefotiam measured by High Performance Liquid Chromatography was 86.8%, and the content of polymer impurities measured by the gel chromatography system was less than 0.1%. To the purified product water was added to prepare a solution of about 0.1 g per 1 ml, which was clear and colorless, with approximately 600 insoluble microparticles having a diameter greater than or equal to 10 μm.

Example 4

10 g expired cefotiam hydrochloride crude drug was taken, where the content of cefotiam measured by High Performance Liquid Chromatography was 75.5%, and the content of polymer measured by a molecular exclusion method was 3.5%. The cefotiam hydrochloride crude product was dissolved in 150 ml water, treated with 25 ml of 1M aqueous sodium bisulfate at a temperature of 50° C. for 4 hours, and then cooled to room temperature. A small amount of precipitates came out, and an aqueous filtrate was obtained after filtration.

To the above aqueous solution ethyl acetate was added for extraction four times, where each time the volume of the solvent used accounted for 30% of the volume of the aqueous solution. The mixture was sufficiently stirred, and allowed to stand. Then the organic phase was separated to obtain an aqueous phase containing cefotiam hydrochloride.

The cefotiam hydrochloride aqueous solution obtained was warmed to 45° C. for being concentrated into a solution volume of 100 ml. Then acetone was added to the aqueous solution at a 4:6 volume ratio of acetone to water. A few cefotiam hydrochloride seed crystals were introduced into the mixture. The mixture slowly cooled to 5° C. for recrystallization. Crystals were precipitated. The mixture was allowed to stand for 20 hours until no further crystals were precipitated. The mixture was centrifuged with a centrifuge, and filtered. The filter cake was washed with acetone, and air-dried to obtain 9.3 g white cefotiam hydrochloride with a yield of 93%.

The content of cefotiam measured by High Performance Liquid Chromatography was 85.3%, and the content of polymer impurities measured by the gel chromatography system was 0.1%. To the purified product, water was added to prepare a solution of about 0.1 g per 1 ml, which was clear and colorless, with approximately 700 insoluble microparticles having a diameter greater than or equal to 10 μm.

The present invention has been described in detail according to the above embodiments. It should be noted that the above embodiments are merely for illustrating the present invention. Without departing from the spirit and essence of the present invention, those skilled in the art can design a variety of alternative and modified embodiments of the present invention, which should be understood as within the protective scope of the present invention.

The invention claimed is:

1. A process for purifying cefotiam hydrochloride, characterized in that it comprises the following steps:
   step 1) dissolving a raw material containing cefotiam hydrochloride in water, treating it with an acidic salt, optionally heating during the treating process, then cooling it, and filtering the precipitate to obtain an aqueous filtrate;
   step 2) adding an ethyl acetate, a cyclohexane or a mixture of ethyl acetate and cyclohexane to the aqueous filtrate for extraction, and then separating the organic phase containing impurities to obtain a purified aqueous solution containing cefotiam hydrochloride; and
   step 3) adding an ethanol or an acetone into the purified aqueous solution, and decreasing the temperature from room temperature to 5° C. for recrystallization, washing the educed crystals by centrifugation, and drying them to obtain a pure cefotiam hydrochloride.

2. The process for purifying cefotiam hydrochloride according to claim 1, characterized in that the acidic salt in step 1) is a sodium bisulfate or a potassium bisulfate.

3. The process for purifying cefotiam hydrochloride according to claim 1, characterized in that the acidic salt in step 1) is sodium bisulfate.

4. The process for purifying cefotiam hydrochloride according to claim 1, characterized in that in step 1), the processing temperature is 30-45° C.; and the processing time ranges from 1 hour to 3 hours.

5. The process for purifying cefotiam hydrochloride according to claim 1, characterized in that in step 2), the ethyl acetate, cyclohexane or mixture of ethyl acetate and cyclohexane for extraction is in an amount less than one-third of the aqueous filtrate, and the extraction is carried out twice or three times.

6. The process for purifying cefotiam hydrochloride according to claims 1, characterized in that in step 3), ethanol is added according to the volume ratio 3:7 of water to ethanol, or acetone is added according to the volume ratio 4:6 of water to acetone.

7. The process for purifying cefotiam hydrochloride according to claim 1, characterized in that in step 3), cefotiam hydrochloride seed crystals are introduced during the recrystallization, and the educed crystals are air-dried.

* * * * *